US011475682B2

(12) United States Patent
Zhou et al.

(10) Patent No.: US 11,475,682 B2
(45) Date of Patent: Oct. 18, 2022

(54) SYSTEM AND METHOD FOR CONTROLLING AN UNMANNED VEHICLE WITH PRESENCE OF LIVE OBJECT

(71) Applicant: SZ DJI TECHNOLOGY CO., LTD., Shenzhen (CN)

(72) Inventors: You Zhou, Shenzhen (CN); Shaojie Shen, Shenzhen (CN); Jiexi Du, Shenzhen (CN); Guyue Zhou, Shenzhen (CN)

(73) Assignee: SZ DJI TECHNOLOGY CO., LTD., Shenzhen (CN)

( * ) Notice: Subject to any disclaimer, the term of this patent is extended or adjusted under 35 U.S.C. 154(b) by 134 days.

(21) Appl. No.: 16/357,895

(22) Filed: Mar. 19, 2019

(65) Prior Publication Data

US 2019/0213391 A1    Jul. 11, 2019

Related U.S. Application Data

(63) Continuation of application No. PCT/CN2016/100358, filed on Sep. 27, 2016.

(51) Int. Cl.
*G06V 20/64* (2022.01)
*B64C 39/02* (2006.01)
*G05D 1/00* (2006.01)
*G05D 1/10* (2006.01)
*G05D 1/04* (2006.01)

(52) U.S. Cl.
CPC .............. *G06V 20/64* (2022.01); *B64C 39/02* (2013.01); *B64C 39/024* (2013.01); *G05D 1/0016* (2013.01); *G05D 1/0033* (2013.01); *G05D 1/0055* (2013.01); *G05D 1/0094* (2013.01); *G05D 1/042* (2013.01); *G05D 1/102* (2013.01); *B64C 2201/127* (2013.01); *B64C 2201/146* (2013.01)

(58) Field of Classification Search
None
See application file for complete search history.

(56) References Cited

U.S. PATENT DOCUMENTS 8,924,044 B1 * 12/2014 Wang ................ A63H 27/02
701/2
2011/0144829 A1    6/2011 Kim et al.
2013/0325244 A1    12/2013 Wang et al.
(Continued)

FOREIGN PATENT DOCUMENTS

CN        104386250 A    3/2015
CN        105120011 A    12/2015
(Continued)

OTHER PUBLICATIONS

World Intellectual Property Organization (WIPO) International Search Report and Written Opinion for PCT/CN2016/100358 dated Jul. 11, 2017 7 Pages.

*Primary Examiner* — Vikkram Bali
(74) *Attorney, Agent, or Firm* — Anova Law Group, PLLC

(57) ABSTRACT

A method for controlling a movable object includes detecting a live object within a proximity of the movable object, determining an operation mode to operate the movable object with the live object detected within the proximity of the movable object, and applying a control scheme associated with the operation mode to control an operation of the movable object.

14 Claims, 10 Drawing Sheets

(56) References Cited

U.S. PATENT DOCUMENTS

| | | | |
|---|---|---|---|
| 2014/0222246 A1* | 8/2014 | Mohamadi | G01S 7/28 |
| | | | 701/2 |
| 2016/0068267 A1 | 3/2016 | Liu et al. | |
| 2016/0229058 A1 | 8/2016 | Pinter et al. | |
| 2017/0174343 A1* | 6/2017 | Erickson | A61B 5/4815 |
| 2018/0194489 A1* | 7/2018 | Harris | H04N 13/271 |

FOREIGN PATENT DOCUMENTS

| | | |
|---|---|---|
| CN | 204868886 U | 12/2015 |
| CN | 105245809 A | 1/2016 |
| CN | 105517666 A | 4/2016 |
| CN | 105931263 A | 9/2016 |
| WO | 2007041295 A2 | 4/2007 |
| WO | 2016065625 A1 | 5/2016 |
| WO | 2016115574 A1 | 7/2016 |

\* cited by examiner

SYSTEM AND METHOD FOR CONTROLLING AN UNMANNED VEHICLE WITH PRESENCE OF LIVE OBJECT

CROSS-REFERENCE TO RELATED APPLICATION

This application is a continuation of International Application No. PCT/CN2016/100358, filed on Sep. 27, 2016, the entire contents of which are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE DISCLOSURE

The disclosed embodiments relate generally to movable object control and more particularly, but not exclusively, to controlling an unmanned vehicle.

BACKGROUND

Unmanned vehicles such as unmanned aerial vehicles (UAVs) can be used for performing surveillance, reconnaissance, and exploration tasks for various applications. Due to the great popularity of UAV and high desirability in the UAV market, more attractive functions needs to be added into the UAV. For example, it is desirable to have the UAV operating in an environment with presence of live objects. This is the general area that embodiments of the disclosure are intended to address.

SUMMARY

Described herein are systems and methods that can control an unmanned vehicle with presence of live object. A controller can detect a live object within a proximity of a movable object. Then, the controller can determine an operation mode to operate the movable object with the live object within the proximity of the movable object. Furthermore, the controller can apply a control scheme associated with the operation mode to control an operation of the movable object.

DETAILED DESCRIPTION

The disclosure is illustrated, by way of example and not by way of limitation, in the figures of the accompanying drawings in which like references indicate similar elements. It should be noted that references to "an" or "one" or "some" embodiment(s) in this disclosure are not necessarily to the same embodiment, and such references mean at least one.

The description of the disclosure as following uses an unmanned aerial vehicle (UAV) as example for a movable object. It will be apparent to those skilled in the art that other types of movable object can be used without limitation.

In accordance with various embodiments of the present disclosure, the system can automatically track and detect a target for a long period of time, e.g. using a movable object such as an unmanned aerial vehicle (UAV), which has limited resource (e.g. both in terms of computing capability and power resource). Additionally, the system can provide re-targeting ability once the target is lost.

Figure 1:
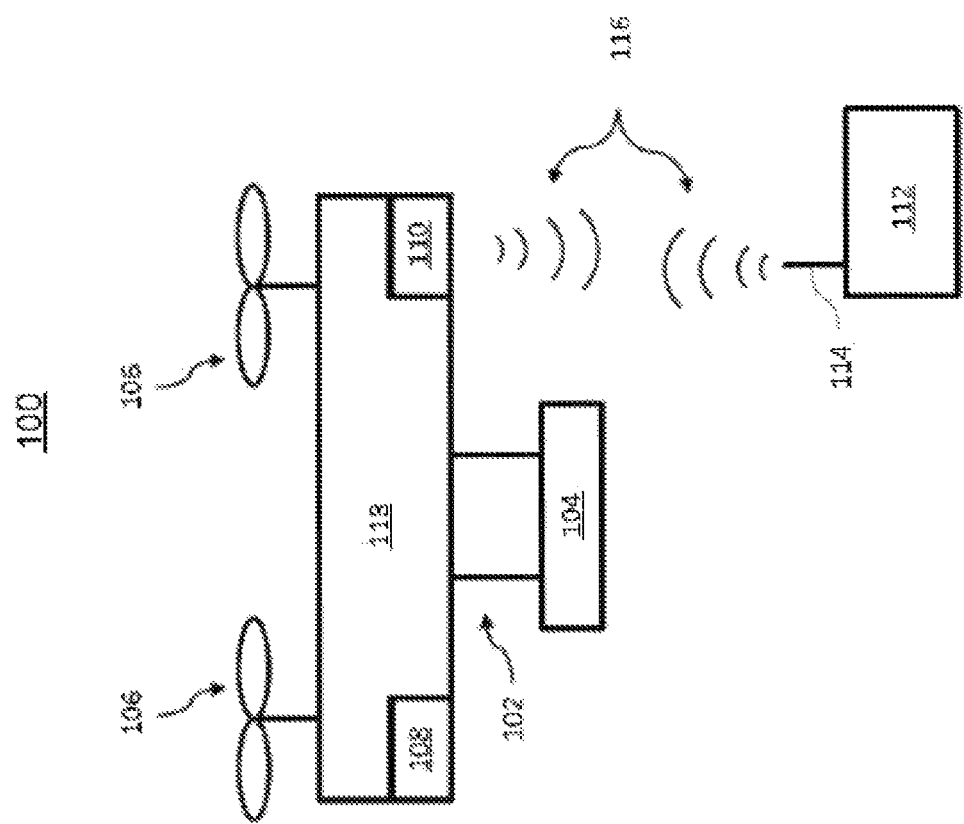
FIG. 1 illustrates a movable object environment, in accordance with various embodiments of the present disclosure.

FIG. 1 illustrates a movable object environment, in accordance with various embodiments of the present disclosure. As shown in FIG. 1, a movable object 118 in a movable object environment 100 can include a carrier 102 and a payload 104. Although the movable object 118 can be depicted as an aircraft, this depiction is not intended to be limiting, and any suitable type of movable object can be used. One of skill in the art would appreciate that any of the embodiments described herein in the context of aircraft systems can be applied to any suitable movable object (e.g., a UAV). In some instances, the payload 104 may be provided on the movable object 118 without requiring the carrier 102.

In accordance with various embodiments of the present disclosure, the movable object 118 may include one or more movement mechanisms 106 (e.g. propulsion mechanisms), a sensing system 108, and a communication system 110.

The movement mechanisms 106 can include one or more of rotors, propellers, blades, engines, motors, wheels, axles, magnets, nozzles, animals, or human beings. For example, the movable object may have one or more propulsion mechanisms. The movement mechanisms 106 may all be of the same type. Alternatively, the movement mechanisms 106 can be different types of movement mechanisms. The movement mechanisms 106 can be mounted on the movable object 118 (or vice-versa), using any suitable means such as a support element (e.g., a drive shaft). The movement mechanisms 106 can be mounted on any suitable portion of the movable object 118, such on the top, bottom, front, back, sides, or suitable combinations thereof.

In some embodiments, the movement mechanisms 106 can enable the movable object 118 to take off vertically from a surface or land vertically on a surface without requiring any horizontal movement of the movable object 118 (e.g., without traveling down a runway). Optionally, the movement mechanisms 106 can be operable to permit the movable object 118 to hover in the air at a specified position and/or orientation. One or more of the movement mechanisms 106 may be controlled independently of the other movement mechanisms. Alternatively, the movement mechanisms 106 can be configured to be controlled simultaneously. For example, the movable object 118 can have multiple horizontally oriented rotors that can provide lift and/or thrust to the movable object. The multiple horizontally oriented rotors can be actuated to provide vertical takeoff, vertical landing, and hovering capabilities to the movable object 118. In some embodiments, one or more of the horizontally oriented rotors may spin in a clockwise direction, while one or more of the horizontally rotors may spin in a counterclockwise direction. For example, the number of clockwise rotors may be equal to the number of counterclockwise rotors. The rotation rate of each of the horizontally oriented rotors can be varied independently in order to control the lift and/or thrust produced by each rotor, and thereby adjust the spatial disposition, velocity, and/or acceleration of the movable object 118 (e.g., with respect to up to three degrees of translation and up to three degrees of rotation).

The sensing system 108 can include one or more sensors that may sense the spatial disposition, velocity, and/or acceleration of the movable object 118 (e.g., with respect to various degrees of translation and various degrees of rotation). The one or more sensors can include any of the sensors, including GPS sensors, motion sensors, inertial sensors, proximity sensors, or image sensors. The sensing data provided by the sensing system 108 can be used to control the spatial disposition, velocity, and/or orientation of the movable object 118 (e.g., using a suitable processing unit and/or control module). Alternatively, the sensing system 108 can be used to provide data regarding the environment surrounding the movable object, such as weather conditions, proximity to potential obstacles, location of geographical features, location of manmade structures, and the like.

The communication system 110 enables communication with terminal 112 having a communication system 114 via wireless signals 116. The communication systems 110, 114 may include any number of transmitters, receivers, and/or transceivers suitable for wireless communication. The communication may be one-way communication, such that data can be transmitted in only one direction. For example, one-way communication may involve only the movable object 118 transmitting data to the terminal 112, or vice-versa. The data may be transmitted from one or more transmitters of the communication system 110 to one or more receivers of the communication system 112, or vice-versa. Alternatively, the communication may be two-way communication, such that data can be transmitted in both directions between the movable object 118 and the terminal 112. The two-way communication can involve transmitting data from one or more transmitters of the communication system 110 to one or more receivers of the communication system 114, and vice-versa.

In some embodiments, the terminal 112 can provide control data to one or more of the movable object 118, carrier 102, and payload 104 and receive information from one or more of the movable object 118, carrier 102, and payload 104 (e.g., position and/or motion information of the movable object, carrier or payload; data sensed by the payload such as image data captured by a payload camera; and data generated from image data captured by the payload camera). In some instances, control data from the terminal may include instructions for relative positions, movements, actuations, or controls of the movable object, carrier, and/or payload. For example, the control data may result in a modification of the location and/or orientation of the movable object (e.g., via control of the movement mechanisms 106), or a movement of the payload with respect to the movable object (e.g., via control of the carrier 102). The control data from the terminal may result in control of the payload, such as control of the operation of a camera or other image capturing device (e.g., taking still or moving pictures, zooming in or out, turning on or off, switching imaging modes, change image resolution, changing focus, changing depth of field, changing exposure time, changing viewing angle or field of view).

In some instances, the communications from the movable object, carrier and/or payload may include information from one or more sensors (e.g., of the sensing system 108 or of the payload 104) and/or data generated based on the sensing information. The communications may include sensed information from one or more different types of sensors (e.g., GPS sensors, motion sensors, inertial sensor, proximity sensors, or image sensors). Such information may pertain to the position (e.g., location, orientation), movement, or acceleration of the movable object, carrier, and/or payload. Such information from a payload may include data captured by the payload or a sensed state of the payload. The control data transmitted by the terminal 112 can be configured to control a state of one or more of the movable object 118, carrier 102, or payload 104. Alternatively or in combination, the carrier 102 and payload 104 can also each include a communication module configured to communicate with terminal 112, such that the terminal can communicate with and control each of the movable object 118, carrier 102, and payload 104 independently.

In some embodiments, the movable object 118 can be configured to communicate with another remote device in addition to the terminal 112, or instead of the terminal 112. The terminal 112 may also be configured to communicate with another remote device as well as the movable object 118. For example, the movable object 118 and/or terminal 112 may communicate with another movable object, or a carrier or payload of another movable object. When desired, the remote device may be a second terminal or other computing device (e.g., computer, laptop, tablet, smartphone, or other mobile device). The remote device can be configured to transmit data to the movable object 118, receive data from the movable object 118, transmit data to the terminal 112, and/or receive data from the terminal 112. Optionally, the remote device can be connected to the Internet or other telecommunications network, such that data received from the movable object 118 and/or terminal 112 can be uploaded to a website or server.

Figure 2:
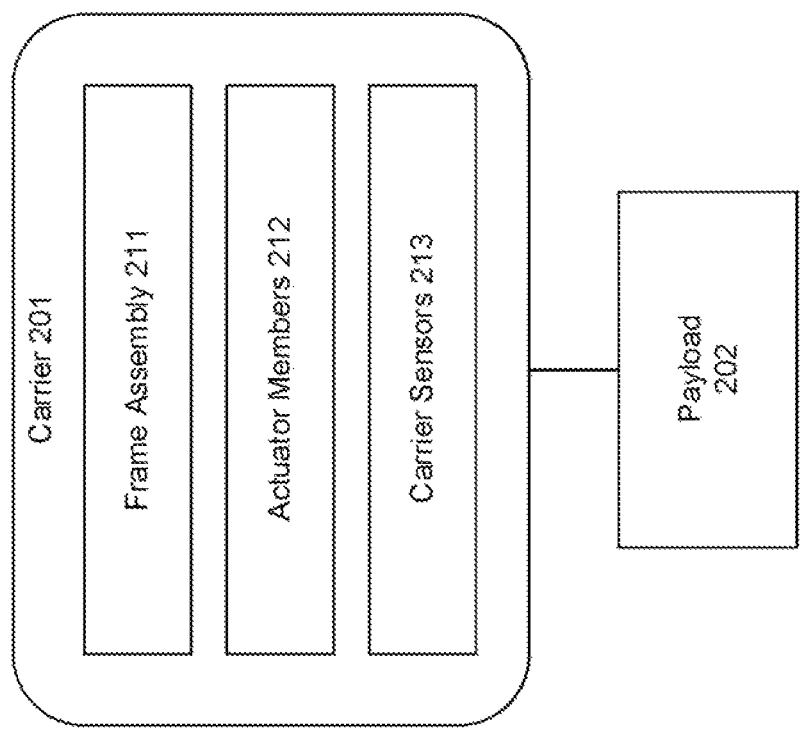
FIG. 2 illustrates an exemplary carrier in a movable object environment, in accordance with embodiments.
Figure 2:
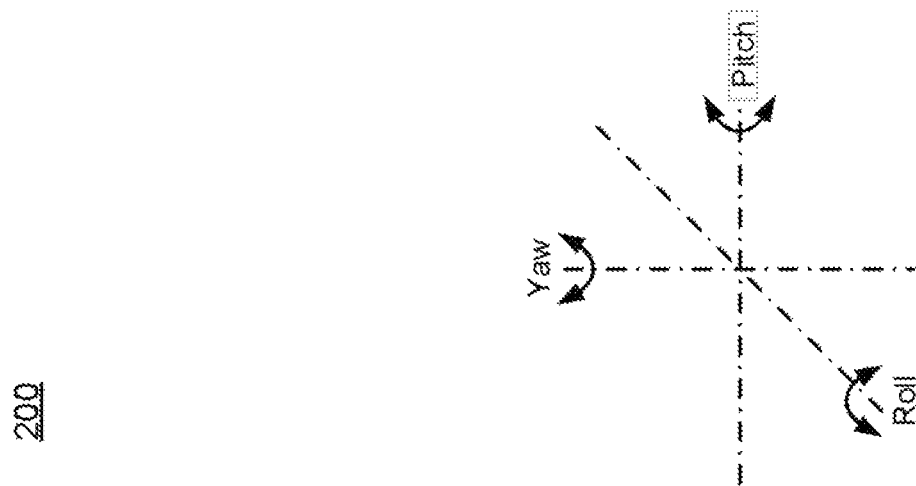

FIG. 2 illustrates an exemplary carrier in a movable object environment, in accordance with embodiments. The carrier 200 can be used to couple a payload 202 such as an image capturing device to a movable object such as a UAV.

The carrier 200 can be configured to permit the payload 202 to rotate about one or more axes, such as three axes: X or pitch axis, Z or roll axis, and Y or yaw axis, relative to the movable object. For instance, the carrier 200 may be configured to permit the payload 202 to rotate only around one, two, or three of the axes. The axes may or may not be orthogonal to each other. The range of rotation around any of the axes may or may not be limited and may vary for each of the axes. The axes of rotation may or may not intersect with one another. For example, the orthogonal axes may intersect with one another. They may or may not intersect at a payload 202. Alternatively, they may not intersect.

The carrier 200 can include a frame assembly 211 comprising one or more frame members. For example, a frame member can be configured to be coupled with and support the payload 202 (e.g., image capturing device).

In some embodiments, the carrier 201 can comprise one or more carrier sensors 213 useful for determining a state of the carrier 201 or the payload 202 carried by the carrier 201. The state information may include a spatial disposition (e.g., position, orientation, or attitude), a velocity (e.g., linear or angular velocity), an acceleration (e.g., linear or angular acceleration), and/or other information about the carrier, a component thereof, and/or the payload 202. In some embodiments, the state information as acquired or calculated from the sensor data may be used as feedback data to control the rotation of the components (e.g., frame members) of the carrier. Examples of such carrier sensors may include motion sensors (e.g., accelerometers), rotation sensors (e.g., gyroscope), inertial sensors, and the like.

The carrier sensors 213 may be coupled to any suitable portion or portions of the carrier (e.g., frame members and/or actuator members) and may or may not be movable relative to the UAV. Additionally or alternatively, at least some of the carrier sensors may be coupled directly to the payload 202 carried by the carrier 201.

The carrier sensors 213 may be coupled with some or all of the actuator members of the carrier. For example, three carrier sensors can be respectively coupled to the actuator members 212 for a three-axis carrier and configured to measure the driving of the respective actuator members 212 for the three-axis carrier. Such sensors can include potentiometers or other similar sensors. In an embodiment, a sensor (e.g., potentiometer) can be inserted on a motor shaft of a motor so as to measure the relative position of a motor rotor and motor stator, thereby measuring the relative position of the rotor and stator and generating a position signal representative thereof. In an embodiment, each actuator-coupled sensor is configured to provide a positional signal for the corresponding actuator member that it measures. For example, a first potentiometer can be used to generate a first position signal for the first actuator member, a second potentiometer can be used to generate a second position signal for the second actuator member, and a third potentiometer can be used to generate a third position signal for the third actuator member. In some embodiments, carrier sensors 213 may also be coupled to some or all of the frame members of the carrier. The sensors may be able to convey information about the position and/or orientation of one or more frame members of the carrier and/or the image capturing device. The sensor data may be used to determine position and/or orientation of the image capturing device relative to the movable object and/or a reference frame.

The carrier sensors 213 can provide position and/or orientation data that may be transmitted to one or more controllers (not shown) on the carrier or movable object. The sensor data can be used in a feedback-based control scheme. The control scheme can be used to control the driving of one or more actuator members such as one or more motors. One or more controllers, which may be situated on a carrier or on a movable object carrying the carrier, can generate control signals for driving the actuator members. In some instances, the control signals can be generated based on data received from carrier sensors indicative of the spatial disposition of the carrier or the payload 202 carried by the carrier 201. The carrier sensors may be situated on the carrier or the payload 202, as previously described herein. The control signals produced by the controllers can be received by the different actuator drivers. Based on the control signals, the different actuator drivers may control the driving of the different actuator members, for example, to effect a rotation of one or more components of the carrier. An actuator driver can include hardware and/or software components suitable for controlling the driving of a corresponding actuator member and receiving position signals from a corresponding sensor (e.g., potentiometer). The control signals can be transmitted simultaneously to the actuator drivers to produce simultaneous driving of the actuator members. Alternatively, the control signals can be transmitted sequentially, or to only one of the actuator drivers. Advantageously, the control scheme can be used to provide feedback control for driving actuator members of a carrier, thereby enabling more precise and accurate rotation of the carrier components.

In some instances, the carrier 201 can be coupled indirectly to the UAV via one or more damping elements. The damping elements can be configured to reduce or eliminate movement of the load (e.g., payload, carrier, or both) caused by the movement of the movable object (e.g., UAV). The damping elements can include any element suitable for damping motion of the coupled load, such as an active damping element, a passive damping element, or a hybrid damping element having both active and passive damping characteristics. The motion damped by the damping elements provided herein can include one or more of vibrations, oscillations, shaking, or impacts. Such motions may originate from motions of the movable object that are transmitted to the load. For example, the motion may include vibrations caused by the operation of a propulsion system and/or other components of a UAV.

The damping elements may provide motion damping by isolating the load from the source of unwanted motion by dissipating or reducing the amount of motion transmitted to the load (e.g., vibration isolation). The damping elements may reduce the magnitude (e.g., amplitude) of the motion that would otherwise be experienced by the load. The motion damping applied by the damping elements may be used to stabilize the load, thereby improving the quality of images captured by the load (e.g., image capturing device), as well as reducing the computational complexity of image stitching steps required to generate a panoramic image based on the captured images.

The damping elements described herein can be formed from any suitable material or combination of materials, including solid, liquid, or gaseous materials. The materials used for the damping elements may be compressible and/or deformable. For example, the damping elements can be made of sponge, foam, rubber, gel, and the like. For example, damping elements can include rubber balls that are substantially spherical in shape. The damping elements can be of any suitable shape such as substantially spherical, rectangular, cylindrical, and the like. Alternatively or in addition, the damping elements can include piezoelectric materials or shape memory materials. The damping elements can include one or more mechanical elements, such as springs, pistons, hydraulics, pneumatics, dashpots, shock absorbers, isolators, and the like. The properties of the damping elements can be selected so as to provide a predetermined amount of motion damping. In some instances, the damping elements may have viscoelastic properties. The properties of the damping elements may be isotropic or anisotropic. For instance, the damping elements may provide motion damping equally along all directions of motion. Conversely, the damping element may provide motion damping only along a subset of the directions of motion (e.g., along a single direction of motion). For example, the damping elements may provide damping primarily along the Y (yaw) axis. As such, the illustrated damping elements can be configured to reduce vertical motions.

Although various embodiments may be depicted as utilizing a single type of damping elements (e.g., rubber balls), it shall be understood that any suitable combination of types of damping elements can be used. For example, the carrier may be coupled to the movable object using one or more damping elements of any suitable type or types. The damping elements may have the same or different characteristics or properties such as stiffness, viscoelasticity, and the like. Each damping element can be coupled to a different portion of the load or only to a certain portion of the load. For instance, the damping elements may be located near contact or coupling points or surfaces of between the load and the movable objects. In some instances, the load can be embedded within or enclosed by one or more damping elements.

Figure 3:
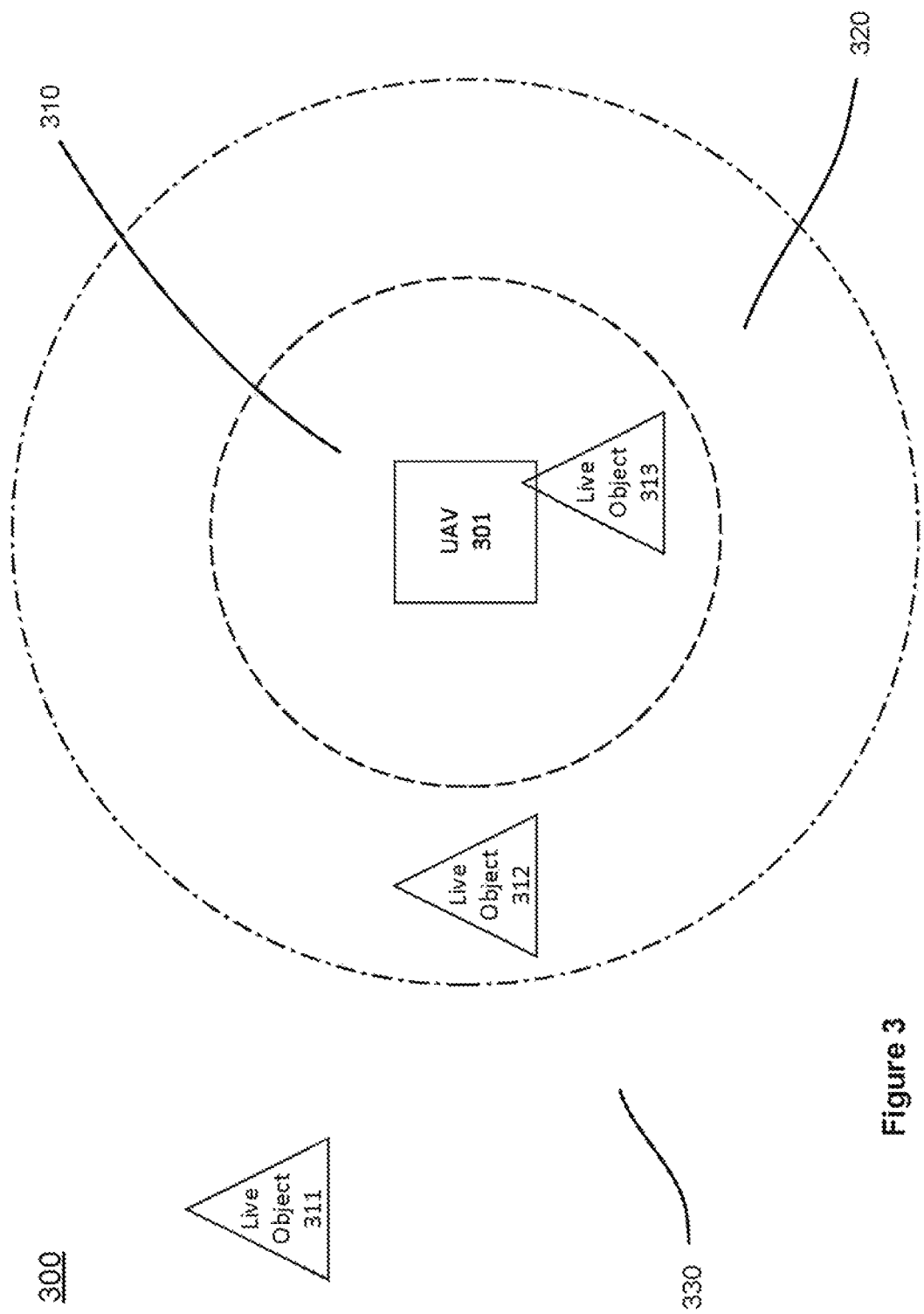
FIG. 3 illustrates controlling UAV movement with presence of one or more live objects, in accordance with various embodiments of the present disclosure.

FIG. 3 illustrates controlling UAV movement with presence of one or more live objects, in accordance with various embodiments of the present disclosure. As shown in FIG. 3, a UAV 301 can detect one or more live objects 311, 312, and 313, which are presented in the UAV operation environment 300. For example, each of the live object 311, 312, or 313 can be a human, an animal, a pet, or any other form of object that is alive. Furthermore, without limitation, a live object 311, 312, or 313 can be any object, such as a robot, which may behave like an object that is alive.

In accordance with various embodiments of the present disclosure, the detection of the live object 311, 312, or 313 can be based on the detection of an environmental change. For example, the UAV 301 can detect a live object 311, 312, or 313 using one or more sensors on-board and/or off-board the UAV 301.

In accordance with various embodiments, the sensors on-board or off board the UAV can collect various types of environmental information. A single sensor may be able to collect a set of information in an environment or a group of sensors may work together to collect a set of information in an environment. Sensors can be used for detection of a live object, in addition to location mapping, navigation between locations, and detection of obstacles. Sensors can also be used for surveillance of an environment or a subject of interest. Sensors can be used for recognizing a live object. The live object may be distinguished from other objects in the environment. Sensors may be used to recognize an object worn or carried by the live object. The worn or carried object may be distinguished from other objects in the environment. Also, the sensors on-board or off board the UAV can collect information such as the location of the live object, the location of the UAV, and the orientation of the UAV.

Various examples of sensors may include, but are not limited to, location sensors (e.g., global positioning system (GPS) sensors, mobile device transmitters enabling location triangulation), vision sensors (e.g., imaging devices capable of detecting visible, infrared, or ultraviolet light, such as cameras), proximity or range sensors (e.g., ultrasonic sensors, LADAR, time-of-flight or depth cameras), inertial sensors (e.g., accelerometers, gyroscopes, inertial measurement units (IMUs)), altitude sensors, attitude sensors (e.g., compasses) pressure sensors (e.g., barometers), audio sensors (e.g., microphones) or field sensors (e.g., magnetometers, electromagnetic sensors). Any suitable number and combination of sensors can be used, such as one, two, three, four, five, or more sensors.

Optionally, data can be received from sensors of different types (e.g., two, three, four, five, or more types). Sensors of different types may measure different types of signals or information (e.g., position, orientation, velocity, acceleration, proximity, pressure, etc.) and/or utilize different types of measurement techniques to obtain data. For instance, the sensors may include any suitable combination of active sensors (e.g., sensors that generate and measure energy from their own energy source) and passive sensors (e.g., sensors that detect available energy). As another example, some sensors may generate absolute measurement data that is provided in terms of a global coordinate system (e.g., position data provided by a GPS sensor, attitude data provided by a compass or magnetometer), while other sensors may generate relative measurement data that is provided in terms of a local coordinate system (e.g., relative angular velocity provided by a gyroscope; relative translational acceleration provided by an accelerometer; relative attitude information provided by a vision sensor; relative distance information provided by an ultrasonic sensor, LADAR, or time-of-flight camera).

In some embodiments, the UAV 301 can have sensors on-board the UAV 301 that collect information directly from an environment. For example, the UAV 301 can detect the presence of a live object 311, 312, or 313, when the vision or audio sensor on-board of the UAV captures images or sounds that indicate the presence of a live object 311, 312, or 313. In some embodiments, such detection can be based on matching one or more observed features of the detected objects with one or more live object signature features, such as the body temperatures and certain movement characteristics.

In one example, the UAV 301 can comprise a vision sensor, e.g. a camera. The vision sensor can be enclosed in the body of the UAV or carried by the UAV as an external payload. For example, when the vision sensor is carried externally as a payload, the vision sensor can be oriented below the body of the UAV. Also, the vision sensor can be attached to the UAV by a carrier. The carrier can be configured such that the vision sensor can rotate and/or tilt relative to the UAV. Also, the carrier permits the vision sensor to translate and/or rotate in three-dimensions. For example, the carrier may permit rotation of the vision sensor about only one or two axes.

In another example, the UAV 301 can comprise an audio sensor. The audio sensor can be enclosed in the body of the UAV 301 or carried by the UAV 301 as an external payload. The audio sensor may be arranged on different parts of the body of the UAV 301, or oriented toward different directions surrounding the UAV 301. Also, the audio sensor can take advantage of a noise filter, which can filter out background noise such as the motor, propeller, or wind noise. Additionally, the audio sensor on-board of the UAV can receive audio signals that are collected by audio receivers installed in the surrounding environment.

In yet another example, the UAV 301 can comprise a thermal sensor. The thermal sensor can be in the body of the UAV 301 or carried by the UAV 301 as an external payload. The thermal sensor can detect the temperature variance in the environment surrounding the UAV 301, e.g. based on infrared light detection. Then, based on the temperature reading and/or related movement characteristics evaluation (e.g. gait recognition), the UAV can be aware of the presence of a live object (e.g. a user) in the surrounding neighborhood.

In some embodiments, the UAV 301 can rely on one or more sensors off-board the UAV for collecting data indicating an environmental change. Various sensors can be installed in the environment where the UAV operates. The UAV can receive the information collected by the sensors off-board the UAV, directly or indirectly, to detect whether a live object is presented in the operation environment, within a proximity of the UAV 301 (e.g. within a predetermined distance threshold from the UAV 301).

In accordance with various embodiments of the present disclosure, the UAV 301 can detect a live object 311 once receiving a signal from the live object 311. For example, the live object 311 can be a user. The user can be at a location, such as a house, yard, room, building, vehicle, or another space or area. The user can communicate with one or more processors on-board the UAV 301 via an electronic device. The electronic device may or may not be a mobile device. The electronic device may or may not be a remote terminal capable of manually controlling flight of the UAV. The electronic device can be in communication with the UAV directly through a wired or wireless connection. The electronic device can further be in communication with a processor, through a wired or wireless connection, the processor can additionally be in communication with the UAV through a wired or wireless connection. Alternatively, the processor may be on-board the electronic device and/or the UAV 301. For instance, the UAV can have one or more on-board processors. The one or more on-board processors can communicate with an external processor and or an electronic device with a user interface. In an example, the communication can be based on a user interface, which can be on an electronic display such as a desktop computer, laptop computer, smart phone, smart watch, smart glasses, tablet, or another device configured to communicate with the one or more processors. The on-board processors may perform any functions of processors described herein. Alternatively, the UAV 301 can communicate directly with the electronic device to communicate with an intermediate device or processor.

In accordance with various embodiments, the UAV 301 can detect the presence of a live object by detecting a signal emitted out from the live object. For example, the live object can carry or be embedded with an electronic device or tag, which can be automatically identified or tracked. For example, such electronic device or tag can be based on the radio frequency identification (RFID), blue tooth, or any near field communication (NFC) technologies. The tags can either passively collect energy from an interrogating RFID reader on-board the UAV 301, or actively emitting signals to the surrounding environment using local power.

In accordance with various embodiments, the live object 104 can optionally have a wearable identifier. For example, the live object can wear a ring, a necklace, a wrist band, or a collar. The UAV vision sensor can detect a visual pattern on the wearable identifier in order to locate the target live object. Alternatively, the wearable identifier can be embedded with an electronic device or tag, which can be electronically identified by a sensor on-board the UAV.

In some embodiments, the detection of the live object 311, 312, or 313 can be achieved by collaborating different sensors, including the sensors on-board the UAV and the sensors off-board the UAV 301. For example, one or more motion detectors can be installed on the ground in the UAV operation environment 300. Once a motion detector detects a live object, such information can be transmitted to the UAV 301, which in turn can confirm the presence of the live object as well as the orientation and distance of the live object relative to the UAV. Additionally, the UAV 301 can refine the detection of the live object by measuring the speed and/or obtaining the dimension of the live object (such as the height of the live object). For example, a thief entering a house may trigger a motion detector, which can inform the UAV. Then, the UAV can initiate a tracking mode and follows the thief based on the measured movement of the thief by sensors on-board the UAV.

In accordance with various embodiments, the UAV 301 in the UAV operation environment 300 can detect a live object, which is presented within a surrounding area of the UAV 301. Furthermore, the surrounding area of the UAV 301 (e.g. the surrounding area of the UAV 301) can be configured as multiple zones. For example, the surrounding area of the UAV 301 can be configured as various operation zones, such as a normal zone, a safe zone, and an interactive zone.

As shown in FIG. 3, the surrounding area of the UAV 301 can be configured as multiple zones 310-330, as defined by a geographic radius. For example, the live object 311 locates at a normal zone 330 (e.g., outside a proximity of the UAV 301), while the live object 312 locates at a safe zone 320 and the live object 313 locates at an interactive zone 310 (e.g., within the proximity of the UAV 301).

In some embodiments, the geographic radius can define a radial region centered at a current location of the UAV 301. Alternatively, the geographic radius can define a radial region centered at a location of a live object, such as a user. In some embodiments, the surrounding area can be defined using various geometry shapes, such as polygons, ellipses and other geometry shapes. User can define a geographic region using global coordinates or local coordinates. In some cases a geographic region can be defined as a region within user defined boundaries, e.g. defined using global coordinates.

In accordance with various embodiments, a user can define the surrounding area of the UAV 301 via a user interface that is in communication with a processor on-board or off-board the UAV 301. The one or more processors can be in communication with one or more memory storage units. The memory storage unit can store past user defined areas. The memory storage device units can store geographic data, such as maps that may optionally be updated. A user can optionally define the surrounding area each time the UAV detects a live object. For example, the surrounding area can be defined as a region in which the live object can safely travel without interfering with the UAV, a boundary past which the live object may interfere with the UAV, and/or a region in which the live object may likely interfere with the UAV.

In various embodiments, a user can provide a visual map. A visual map can be generated in a user interface on an electronic device. The user interface can provide a map of a chosen or local space in which a live object can interact with the UAV. A user can mark areas, which are permissible or impermissible for the UAV and/or the live object to travel, on the map provided by the user interface. In some cases, a user can mark areas on the map using a touch screen provided on the user interface. A user's finger or a pointer (e.g., mouse pointer, trackball pointer, etc.) may be used to trace the outline of boundaries. The user can draw circles on the user interface to define an area. Alternatively, the user can click on or touch points to define the coordinates of a region.

In accordance with various embodiments, one or more processors on-board the UAV 301 can monitor the live object while receiving one or more location signals on-board or off-board the UAV. For example, the UAV can automatically track and detect a target live object for a long period of time, e.g. using a movable object such as an unmanned aerial vehicle (UAV), which has limited resource (e.g. both in terms of computing capability and power resource). Additionally, the system can provide re-targeting ability once the target live object is lost.

In accordance with various embodiments, the UAV 301 can change the operation mode after the detection of the live object. Such determination can be based on the distance, velocity or other factors. For example, the UAV 301 can be in a normal operation mode when it is operating in a normal zone. Alternatively, the UAV 301 can be in a safe operation mode when the UAV is operating in a safe zone, and the UAV 301 can be in an interactive operation mode when the UAV is in an interactive zone. In some embodiments, the UAV 301 can change the operation mode after the detection of the live object. Such determination can be based on the distance, velocity and/or other factors. Furthermore, the determination of the operation mode can be based on the environmental type. In some embodiments, the configuration of the zones can be effected by the factors such as whether the UAV is within an indoor environment or an outdoor environment. For example, the operation zones can be defined using a larger radius or in a regular shape when the UAV is operating in an outdoor environment. On the other hand, the operation zones can be defined using a smaller radius or in an irregular shape when the UAV is operating in an indoor environment.

Figure 4:
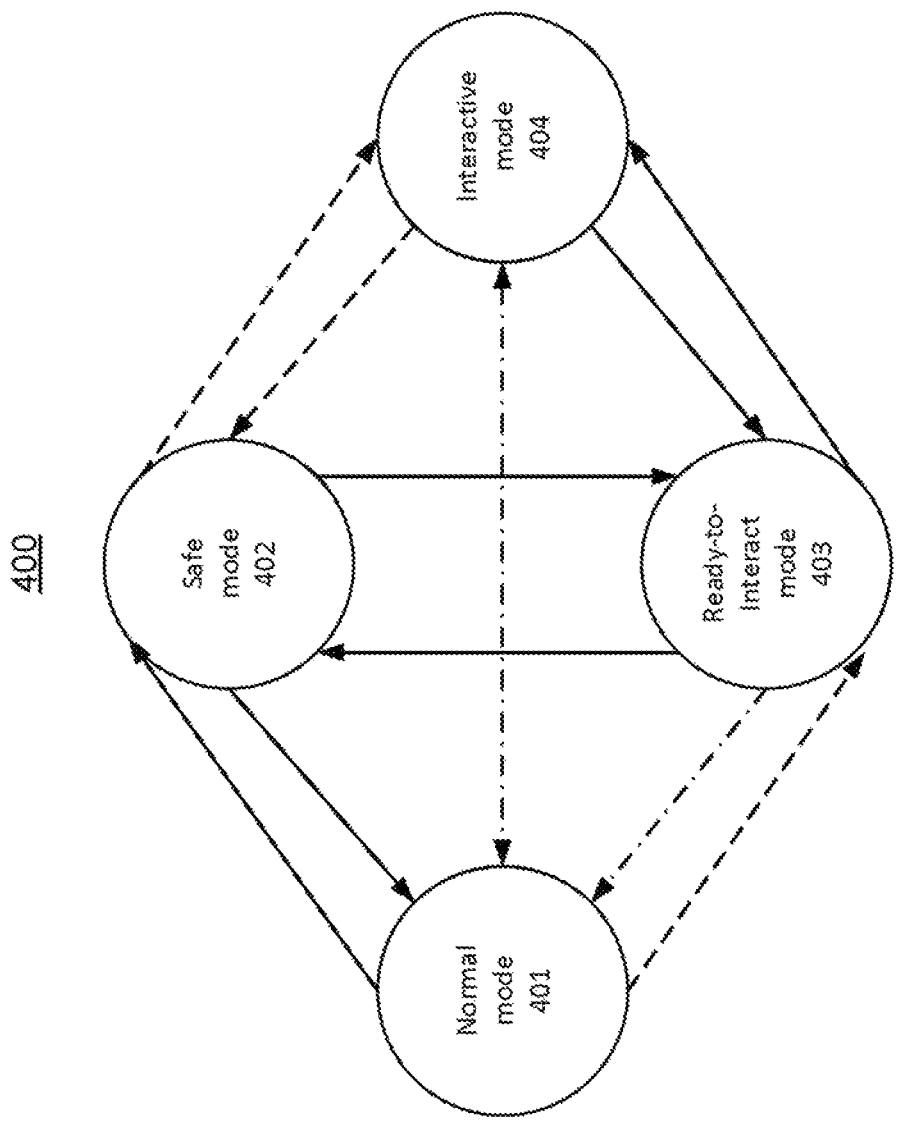
FIG. 4 shows an exemplary diagram for illustrating transitions among various UAV operation modes, in accordance with various embodiments of the present disclosure.

FIG. 4 shows an exemplary diagram for illustrating transitions among various UAV operation modes, in accordance with various embodiments of the present disclosure. As shown in FIG. 4, the UAV 400 can be configured to operate in various operation modes 401-404.

For example, the UAV 400 can be operating in a normal mode 401 when no live object is detected, or locates in a normal zone. On the other hand, when the UAV 400 detects a live object within the proximity of the UAV 400 (e.g. a safe zone), the UAV 400 can transit into a safe mode 402. In such a case, the UAV 400 can apply various safety scheme in order to safely, reliably and conveniently operate the UAV 400. For example, such safety scheme may include limiting the movement speed of the UAV 400 for preventing collision with the live object or controlling the UAV 400 into a hovering state.

Furthermore, the UAV 400 can transit into a ready-to-interact mode 403, after the UAV 400 determines that a user shows an intention to interact with the UAV, e.g. by moving closer toward the UAV 301 or waving a hand. In some embodiments, when the UAV 301 is in a ready-to-interact mode, the UAV 301 can make itself ready for the interaction.

In accordance with various embodiments, the UAV can employ different mechanisms for supporting the interaction with a live object, such as a user. For example, the UAV can stay steady (i.e. remain hovering) for user interaction. Thus, a user can press a button on the body of the UAV. Additionally, the UAV can raise the rotor to allow for easy access by the user.

As shown in FIG. 4, the UAV 400 can enter an interactive mode 404 (e.g. from the ready-to-interact mode 403), as soon as the user starts (or about) to interact with the UAV 400. In accordance with various embodiments, the UAV can employ a different control scheme or reconfigure the control scheme for supporting the interaction between the live object and the UAV 400. Alternatively, the UAV can transit directly from the safe mode 402 to the interaction mode 404.

Once the user finishes interacting with the user, or if the user decides not to interact with the UAV (e.g., by moving away from the UAV), the UAV can return to the safe mode 402 before returning to the normal mode 401. Alternatively, the UAV may transit from the interactive mode 404 to the ready-to-interact mode 403, so that the UAV can remain ready (or prepared) for the interaction by the live object. For example, if the user re-engages with the UAV, the UAV may transit from the ready-to-interact mode 403 to the interactive mode 404.

Furthermore, the UAV can transit from the safe mode 402 into the normal mode 401, when the live object decides not to interact with the UAV or is incapable of interacting with the UAV (e.g. when the live object is at a substantial distance away from the UAV).

Figure 5:
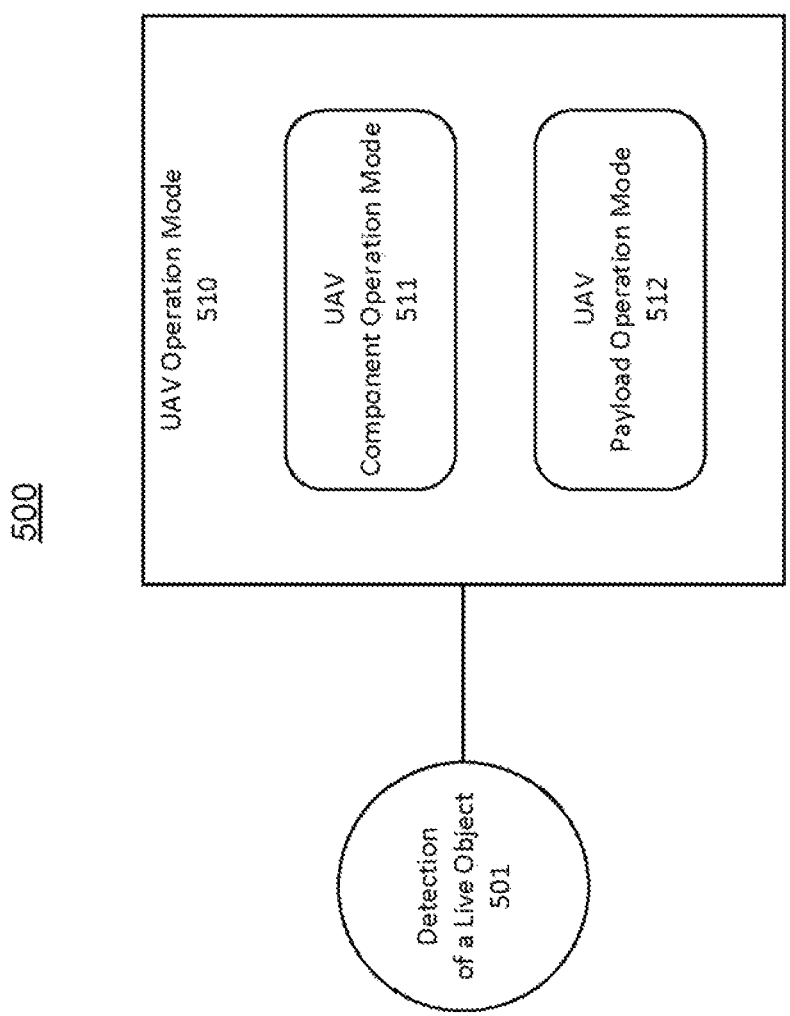
FIG. 5 illustrates an exemplary UAV operation mechanism, in accordance with various embodiments of the present disclosure.

FIG. 5 illustrates an exemplary UAV operation mechanism, in accordance with various embodiments of the present disclosure. As shown in FIG. 5, a UAV 500 can be configured to operate in a UAV operation mode 510. The UAV operation mode 501 can determine how the UAV 500 operates under a particular circumstance, e.g. after a detection of a live object 501. For example, the UAV 500 can be configured to take certain safety measures when the UAV 500 is operating in a safe mode. Alternatively, the UAV can be in a ready-to-interact node in order to prepare for entering into an interactive mode. In some embodiments, the system can apply a first component operation mode (e.g. a safe mode) when the live object is detected within the proximity of the movable object, and can apply a second component operation mode (e.g. a normal mode) when no live object is detected within the proximity of the movable object, and wherein the first component operation mode and the second component operation mode are different.

In accordance with various embodiments, when the UAV 500 is operating in a UAV operation mode 510, the UAV 500 can be configured to operate in a UAV component operation mode 502. The UAV component operation mode 502 can be configured differently for various components on-board the UAV 500, such as sensors, rotors, and motors, corresponding to the different UAV operation modes 501. Additionally, the set of UAV components that may adopt the UAV component operation mode can be preselected or predefined. For example, when the UAV is operating in an interactive mode, a set of components such as the vision sensors and the ultrasonic radar may be configured to operate in an interactive mode, while the barometer and the inertial measurement unit remains operating in the normal mode. In some embodiments, when the operation of the UAV 500 transits into an interactive mode, the operation of the UAV components can adjust accordingly in order for supporting the interactive mode. For example, the operation of the UAV opponent, such as the sensor on-board the UAV, can adopt a UAV component operation mode, since the operation of the sensor may be interfered by the live object.

In accordance with various embodiments, the UAV can take advantage of different UAV component operation modes 502 that employ different control logics, when the operation of the UAV transits among different operation modes. In some embodiments, when the UAV is operating in an interactive mode or a ready-to-interact mode, the measurement of a vision senor or an ultrasonic sensor may be interfered. For example, when a user is holding or touching the UAV from underneath in the interactive mode, the measurement by the sensors, which are mounted at the bottom of the UAV, may be corrupted and not trustworthy when the sensor is blocked by a user's hand. The UAV can employ a logic that can exclude or modify the measurement (e.g. data hopping) by the interfered sensors. For example, the system can choose to trust and use the measurement by the sensors that are not interfered, such as the sensors mounted on top of the UAV or a different type of sensors such as the barometer or the inertia measurement unit (IMU).

In accordance with various embodiments, when the UAV 500 is operating in a UAV operation mode 501, the UAV 500 can be configured to operate in a UAV payload operation mode 512. For example, the system can apply a first payload operation mode (e.g. a safe mode) when the live object is detected within the proximity of the movable object, and can apply a second payload operation mode (e.g. a normal mode) when no live object is detected within the proximity of the movable object, and wherein the first payload operation mode and the second payload operation mode are different.

In some embodiments, the UAV payload operation mode 512 can be configured differently for the different UAV operation modes 501. In some embodiments, the payload (e.g. a camera), which is attached to the UAV 500, can operate correspondingly to the operation mode of the UAV 500, e.g. by adopting a corresponding UAV payload operation mode. For example, when the UAV 500 is operating in a normal mode, the control logic for a carrier that carries the payload, such as a camera, can stabilize the camera for facing a certain direction. On the other hand, when the UAV 500 enters an interactive mode, the control logic for the carrier may allow the user to freely rotate the camera to point to a random direction that is desirable.

Figure 6:
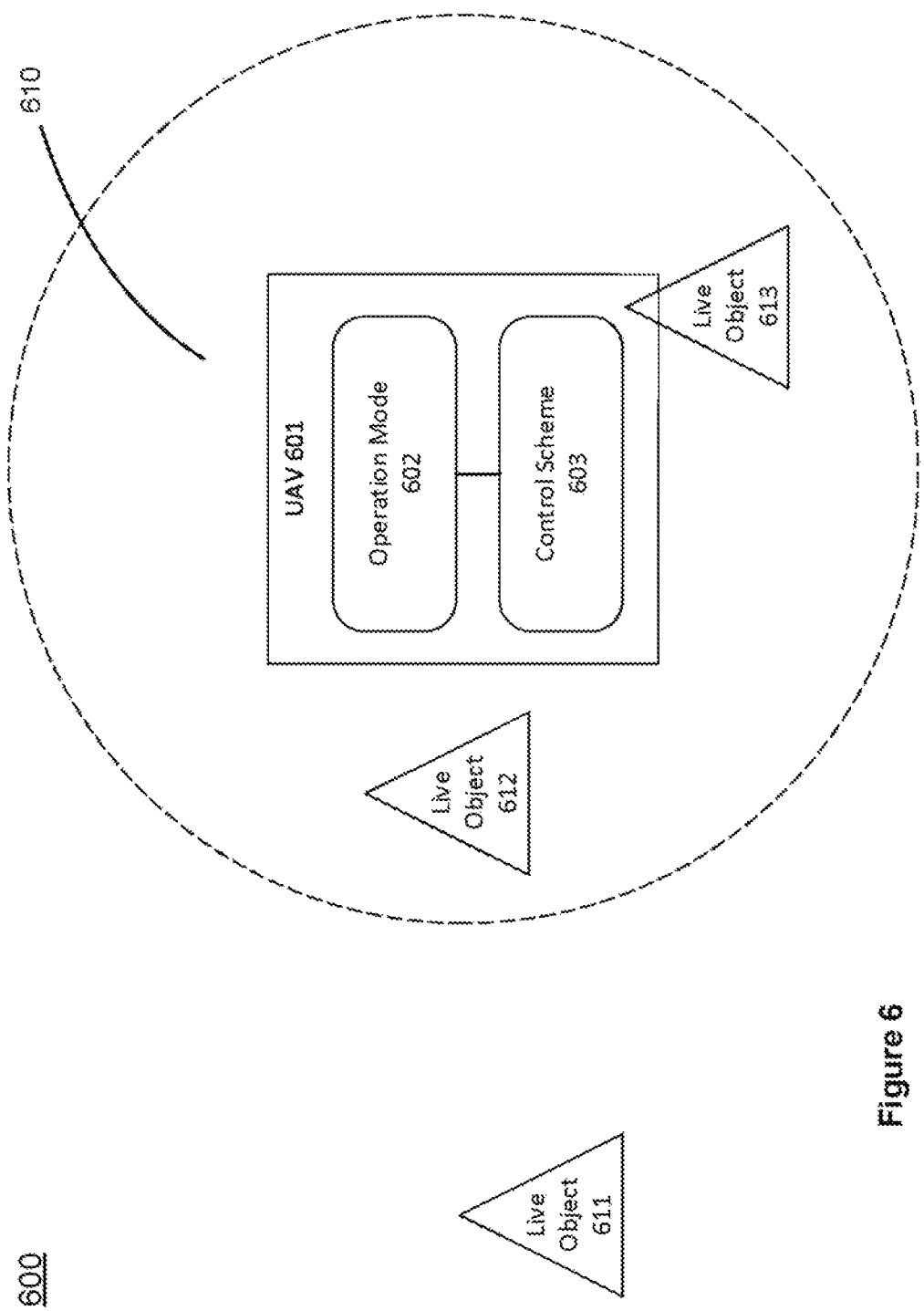
FIG. 6 illustrates supporting interaction between a live object and a UAV, in accordance with various embodiments of the present disclosure.

FIG. 6 illustrates supporting interaction between a live object and a UAV, in accordance with various embodiments of the present disclosure. As shown in FIG. 6, a UAV 601 can associate an operation mode 602 with a control scheme 603. For example, the control scheme 603 can be based on various control methodologies, such as a proportional-integral-derivative (PID) control scheme.

In accordance with various embodiments, the UAV 601 can be configured to behave differently for different operation modes. For instance, different control schemes 603 can be employed for configuring the UAV in different operation modes 602. Alternatively, a control scheme 603 can be used for handling different operation modes.

As shown in FIG. 6, when a live object 611 is detected outside of a proximity 610 of the UAV 601, the UAV 601 can be operating in a normal operation mode. In such a case, the UAV 601 can employ a normal control scheme for controlling various movement characteristics of the UAV 601 (e.g. the position, the velocity, the orientation, and the tilt of the UAV 601). Correspondingly, a predetermined or selected set of UAV components and payloads can operate in a normal operating mode. On the other hand, when the live object 612 moves into the proximity 610 of the UAV 601, the UAV 601 can be operating in a safe mode or a ready-to-interact mode. In such a case, the UAV 601 can employ a control scheme that can control the movement characteristics of the UAV in a different fashion. For example, the UAV 601 can apply a speed limit or enter into a hovering state. Additionally, when the live object 613 operates in an interactive mode, the component, such as sensors on-board the UAV 601 and the payload carried by the UAV, can operate in corresponding interactive mode.

In accordance with various embodiments, the UAV 601 can be configured to employ different control schemes corresponding to different operation modes. For example, under a first operation mode, the system may allow a user to rotate the UAV 601 with respect to two axes. On the other hand, the system may allow a user to rotate the UAV 601 with respect to all three axes under a second operation mode. Furthermore, the UAV 601 can be configured to employ different control schemes corresponding to different live objects. For example, by taking advantage of various gait recognition techniques, the UAV 601 can be aware of different types of live objects (e.g. distinguishing between a user and a pet). Also, the system can assign different roles and/or associate different privileges with the different users based on different user profiles. For example, an adult user may have a full control of the UAV 601 while a kid user may only have a subset of the capability. Additionally, the UAV 601 can be configured to employ different control schemes based on various additional factors, such as the environmental types (e.g., indoor/crowded vs. outdoor/sparse space) and state of the UAV or components thereof (e.g., altitude, velocity, orientation, battery life, sensor status). Moreover, the correspondence of the various control schemes to the different operation modes can be rule-based, which are configurable in real-time.

Figure 7:
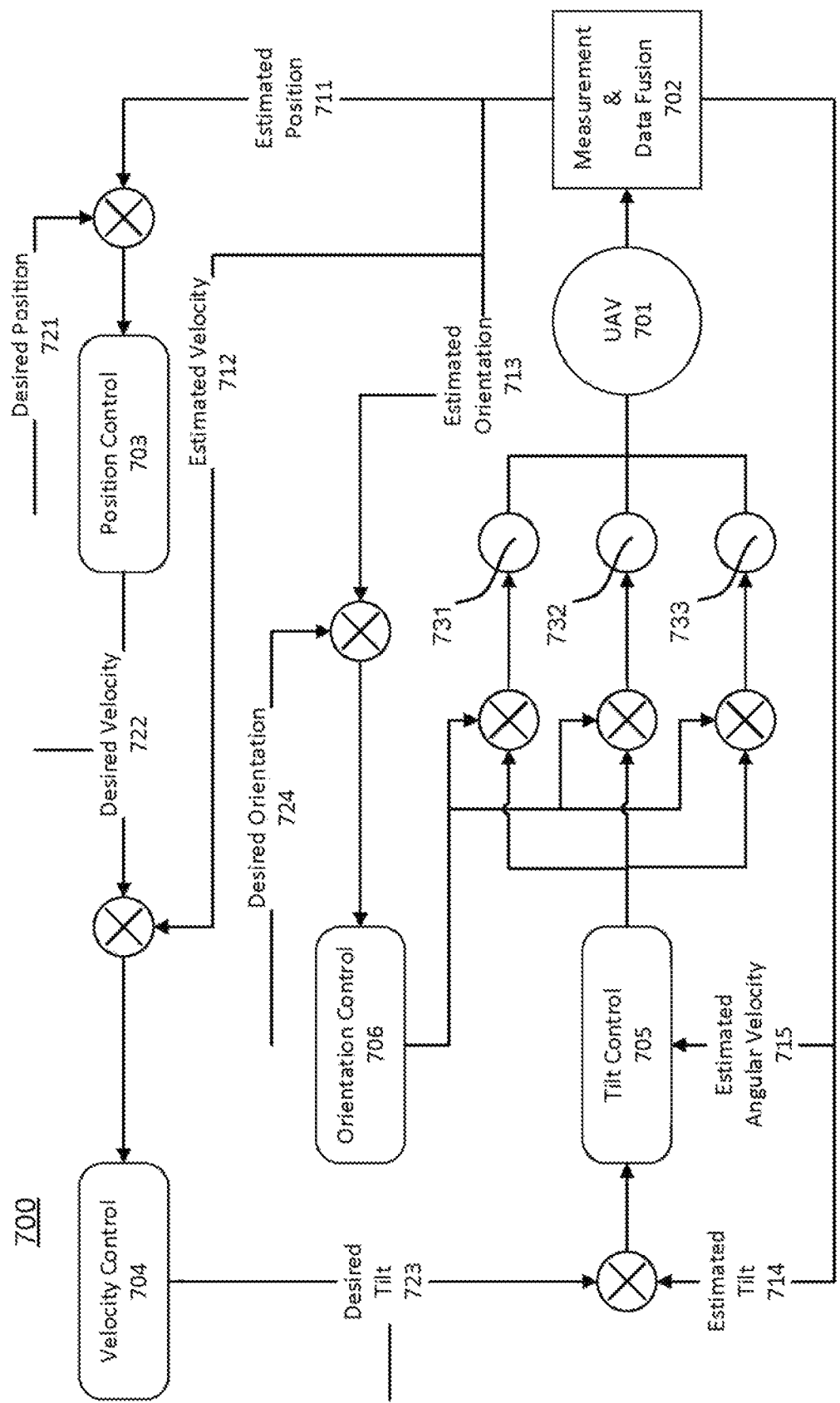
FIG. 7 illustrates an exemplary control scheme for controlling a UAV, in accordance with various embodiments of the present disclosure.

FIG. 7 illustrates an exemplary control scheme for controlling a UAV, in accordance with various embodiments of the present disclosure. As shown in FIG. 7, a UAV 701 can employ a control scheme 700 that includes a position control component 703, a velocity control component 704, a tilt control component 705, and an orientation control component 706.

In accordance with various embodiments, a sensing system on the UAV 701 can measure the state of the UAV 701. Additionally, the system can obtain the estimated flight status based on various data fusion techniques 702. The sensing system can obtain the measured UAV position, velocity, orientation, tilt, and angular velocity. For example, a GPS sensor can obtain the estimated position of the UAV 701, an IMU, which may include a gyroscope, accelerometer, and magnetometer can obtain the estimated acceleration and angular velocity of the UAV 701, as well as the estimated orientation of the UAV 701.

In accordance with various embodiments, the control scheme 700 can be adjusted for controlling the UAV 701 in different circumstances. For example, in order to maintain the UAV 701 hovering at a fixed position or traveling along a desired path, the position control component 703 can generate a desired velocity 722 to counter any drift movement of the UAV 701 away from its desired position 721. Furthermore, the velocity control component 704 can generate desired tilt 723 for achieving the desired velocity 722. Then, the tilt control component 705 can generate motor control signals for achieving the desired tilt 723 based on the estimated tilt 714 and estimated angular velocity 715. Such motor control signals can be used for controlling the various movement mechanics 731-733 associated with the UAV 701.

As shown in FIG. 7, a position control component 703 can obtain a desired velocity 722 based on the difference of the desired position 721 and the estimated position 711. Also, a velocity control component 704 can obtain the desired tilt 723 based on the difference between the desired velocity 722 and the estimated velocity 712. Additionally, a title control component 705 can calculate the motor control signals based on the estimated angular velocity 715 and the difference between the desired tilt 723 and the estimated tilt 714.

Also, the UAV 701 can maintain a fixed orientation or a desired orientation, the orientation control component can generate motor control signals for generating a force that can counter any drift of the UAV orientation. Also as shown in FIG. 7, an orientation control component 706 can generate the motor control signals based on the difference between the desired orientation 724 and the estimated orientation 713. Thus, the combined or integrated motor control signals can be used for controlling the various movement mechanics 731-733 associated with the UAV 701, the movement characteristics of which can be measured and can be used for generating further control signals for controlling the UAV 701 in real-time.

In accordance with various embodiments, the control scheme 700 can be configured for different operation modes. For example, the system can limit the control gain in the orientation control component 706, so that when the user applies a force on the UAV from a side direction (e.g. a yaw direction), the UAV 701 can turn as the user desires. On the other hand, if the control scheme is not modified, the UAV 701 can generate a resistance force for maintaining the UAV 701 in an instant orientation.

In accordance with various embodiments, the system can limit the control gain in the position control component 703 in a similar fashion, so that when the user applies a force on the UAV 701 from a side direction, the UAV 701 can move to different location as the user desires. On the other hand, if the control scheme is not modified, the UAV 701 can generate a resistance force that may try to maintain an instant location.

Figure 8:
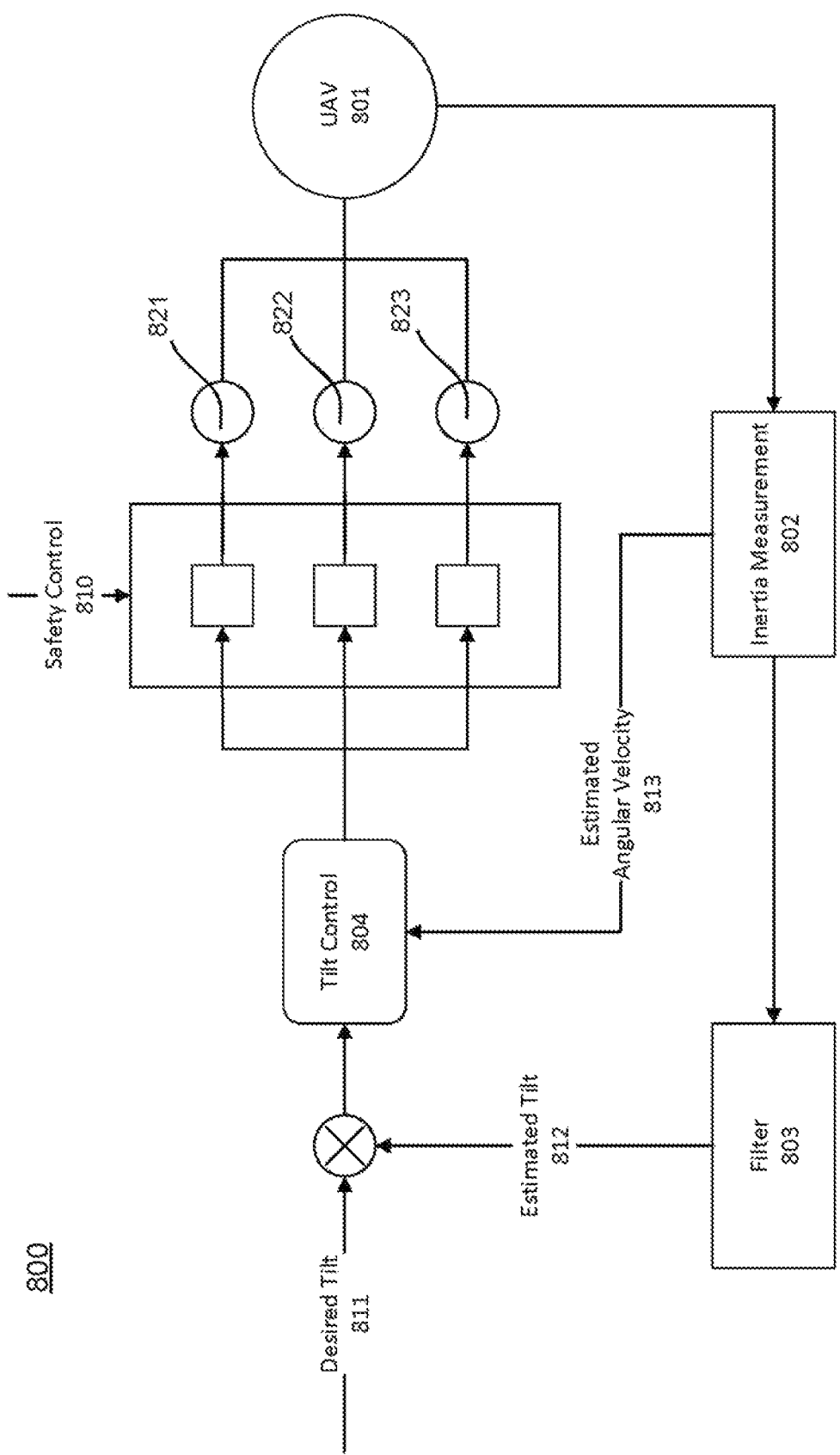
FIG. 8 illustrates an exemplary control scheme for supporting an interactive mode, in accordance with various embodiments of the present disclosure.

FIG. 8 illustrates an exemplary control scheme for supporting an interactive mode, in accordance with various embodiments of the present disclosure. As shown in FIG. 8, UAV 801 can employ a control scheme 800 that includes a tilt control component 804, while limiting control gains for other control components (not shown).

In accordance with various embodiments, the UAV 801 can obtain the estimated tilt 812 based on different measured states of the UAV. For example, an inertia measurement module 802 on the UAV 801 can measure the state of the UAV, such as an angular velocity measured by a gyroscope and a tilt measured by an accelerometer. The estimation can be based on a filter 803 that is capable of performing data fusion of different types of the measurement. Then, based on the difference between the desired tilt 811 and estimated tilt 812, the tilt control component 804 can determine the expected control signal for the motors 821-823 of the UAV 801.

In accordance with various embodiments, a safety control mechanism 810 can be applied in the control scheme so that the UAV 801 can operate in a safe, reliable and convenient fashion. In some embodiments, the UAV can direct the motor to stop moving as soon as it detects an abnormal condition. For example, the safety control mechanism 810 can direct the motor to stop running, as soon as the UAV detects a sudden rise in the current in motor, which may indicate a potential motor stalling (a condition when the motor stops rotating). The stalling condition occurs when the load torque is greater than the motor shaft torque (e.g., in a collision situation). In the stalling condition, the motor draws maximum current but the motor does not rotate.

Figure 9:
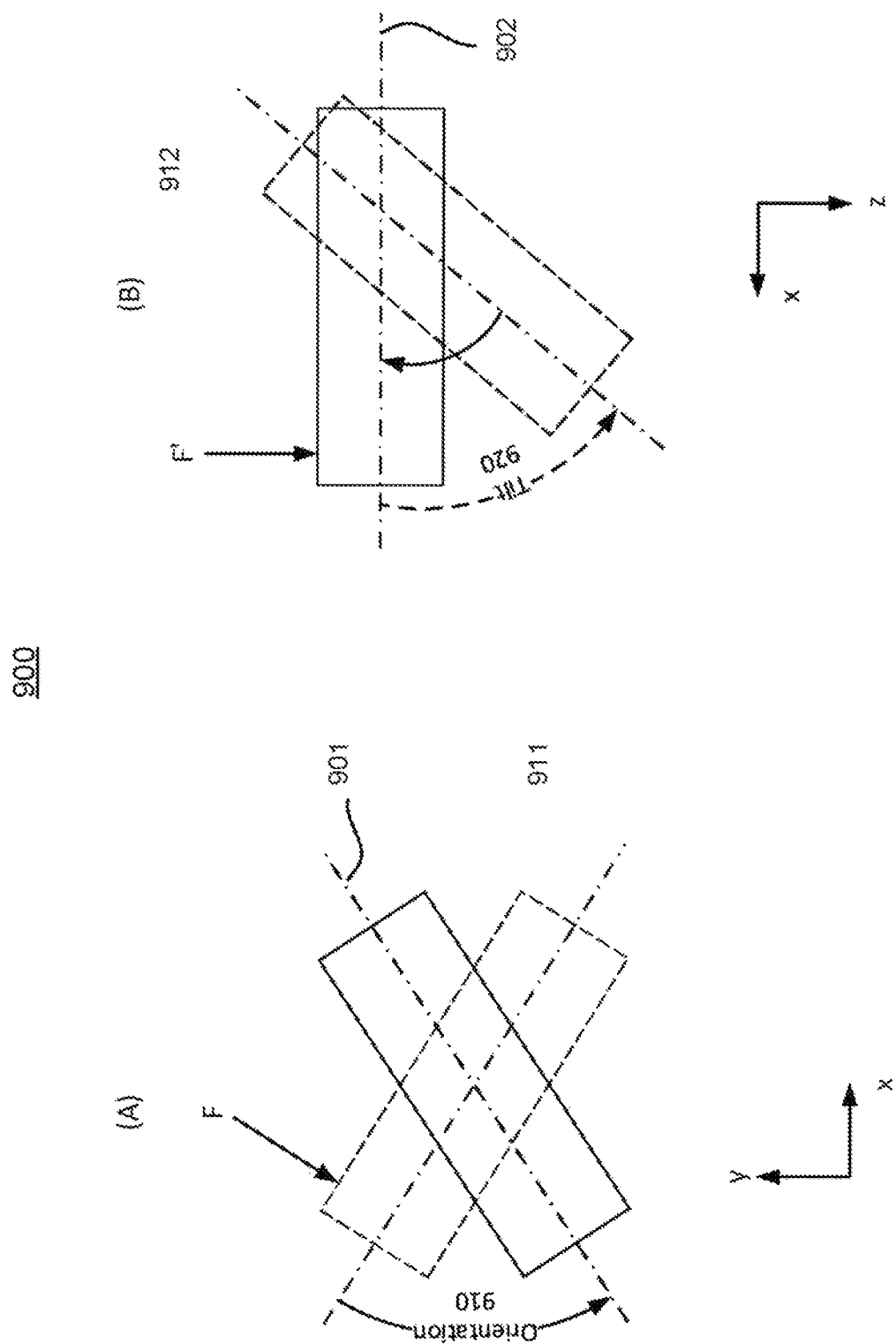
FIG. 9 illustrates controlling an UAV in an interactive mode, in accordance with various embodiments of the present disclosure.

FIG. 9 illustrates controlling an UAV in an interactive mode, in accordance with various embodiments of the present disclosure. A control scheme 900 can be employed for maintaining a UAV in a horizontal plane while allowing a user to freely rotate the UAV to a desired orientation or to freely move the UAV to a desired location, in an interactive mode.

As shown in FIG. 9A, a force F can be applied along a yaw direction in order to adjust the orientation 901 of the UAV in a horizontal plane (e.g. an x-y plane). After the release of the force F, the UAV may stay at the orientation 911 as a result of applying the force F by the user. Thus, the user can freely rotate the UAV to a desired orientation, e.g. for the purpose of taking a picture or monitoring a pet.

On the other hand, as shown in FIG. 9B, a user may apply a force F' along a vertical direction (e.g. in an x-z plane) to hold the UAV at a titling position 912. Once the force F' is released, the UAV can return to the original horizontal attitude 902, since the title control component in the control scheme can generate a counter force to return the UAV to the horizontal position. Hence, the control scheme 900 can prevent the UAV from drifting away in a horizontal direction (since the UAV may move horizontally while in a tilting position). As a result, the UAV can be maintained in a tightly controlled space and can avoid collision with the surrounding objects such as a live object.

In accordance with various embodiments, when a random force is applied on the UAV, the control scheme 900 can be configured to respond to only a component (or portion) of the applied force. For example, using the control scheme as shown in FIG. 8, only the yaw component of the applied force may take effect while a counter force may be generated to maintain the UAV in a horizontal attitude. In other words, the UAV can be configured to allow a user to freely rotate the UAV along a yaw direction and to return to the horizontal attitude once the force is released. Thus, the UAV may be prevented from drifting away in a horizontal direction, which is unfavorable and can be dangerous due to the presence of the live object (e.g. for avoiding hitting the user).

In some embodiments, the control scheme 900 can be configured in various different fashions. For example, the UAV can be configured to maintain the yaw and pitch attitude while allow a user to rotate the UAV about a roll axis. Also, the UAV can be configured to maintain the yaw and roll attitude while allow a user to rotate the UAV along a pitch direction. Alternatively, the UAV can be configured to maintain only one of the yaw, roll and pitch attitude while allow a user to rotate the UAV about other two axes.

In accordance with various embodiments, similar control scheme can be applied on the payload or component on-board the UAV. For example, a user can first move the UAV to a particular location with a particular orientation. Then, the user can adjust the camera carried by the UAV to point to a particular direction in order for taking a picture (by limiting control gains of various control components for the carrier, e.g. a gimbal).

Figure 10:
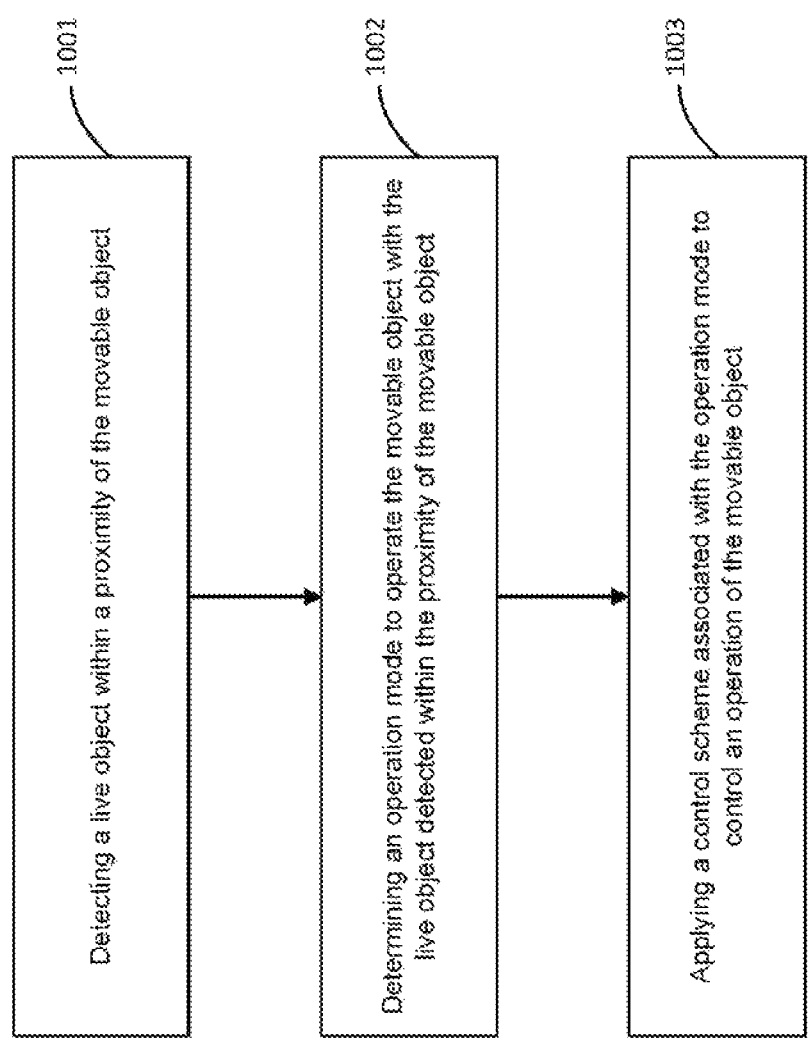
FIG. 10 shows a flowchart of controlling a movable object with presence of a live object in a movable object environment, in accordance with various embodiments of the present disclosure.

FIG. 10 shows a flowchart of controlling a movable object with presence of a live object in a movable object environment, in accordance with various embodiments of the present disclosure. As shown in FIG. 10, at step 1001, the system can detect a live object within a proximity of a movable object. Then, at step 1002, the system can determine an operation mode to operate the movable object with the live object within the proximity of the movable object. Furthermore, at step 1003, the system can apply a control scheme associated with the operation mode to control an operation of the movable object.

Many features of the present disclosure can be performed in, using, or with the assistance of hardware, software, firmware, or combinations thereof. Consequently, features of the present disclosure may be implemented using a processing system (e.g., including one or more processors). Exemplary processors can include, without limitation, one or more general purpose microprocessors (for example, single or multi-core processors), application-specific integrated circuits, application-specific instruction-set processors, graphics processing units, physics processing units, digital signal processing units, coprocessors, network processing units, audio processing units, encryption processing units, and the like.

Features of the present disclosure can be implemented in, using, or with the assistance of a computer program product which is a storage medium (media) or computer readable medium (media) having instructions stored thereon/in which can be used to program a processing system to perform any of the features presented herein. The storage medium can include, but is not limited to, any type of disk including floppy disks, optical discs, DVD, CD-ROMs, microdrive, and magneto-optical disks, ROMs, RAMs, EPROMs, EEPROMs, DRAMs, VRAMs, flash memory devices, magnetic or optical cards, nanosystems (including molecular memory ICs), or any type of media or device suitable for storing instructions and/or data.

Stored on any one of the machine readable medium (media), features of the present disclosure can be incorporated in software and/or firmware for controlling the hardware of a processing system, and for enabling a processing system to interact with other mechanism utilizing the results of the present disclosure. Such software or firmware may include, but is not limited to, application code, device drivers, operating systems and execution environments/containers.

Features of the disclosure may also be implemented in hardware using, for example, hardware components such as application specific integrated circuits (ASICs) and field-programmable gate array (FPGA) devices. Implementation of the hardware state machine so as to perform the functions described herein will be apparent to persons skilled in the relevant art.

Additionally, the present disclosure may be conveniently implemented using one or more conventional general purpose or specialized digital computer, computing device, machine, or microprocessor, including one or more processors, memory and/or computer readable storage media programmed according to the teachings of the present disclosure. Appropriate software coding can readily be prepared by skilled programmers based on the teachings of the present disclosure, as will be apparent to those skilled in the software art.

While various embodiments of the present disclosure have been described above, it should be understood that they have been presented by way of example, and not limitation. It will be apparent to persons skilled in the relevant art that various changes in form and detail can be made therein without departing from the spirit and scope of the disclosure.

The present disclosure has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the disclosure.

The foregoing description of the present disclosure has been provided for the purposes of illustration and description. It is not intended to be exhaustive or to limit the disclosure to the precise forms disclosed. The breadth and scope of the present disclosure should not be limited by any of the above-described exemplary embodiments. Many modifications and variations will be apparent to the practitioner skilled in the art. The modifications and variations include any relevant combination of the disclosed features. The embodiments were chosen and described in order to best explain the principles of the disclosure and its practical application, thereby enabling others skilled in the art to understand the disclosure for various embodiments and with various modifications that are suited to the particular use contemplated. It is intended that the scope of the invention be defined by the following claims and their equivalence.

What is claimed is:

1. A method for controlling a movable object, comprising:
determining whether a user of the movable object is within a proximity of the movable object;
in response to detecting the user being within a proximity of the movable object, switching an operation mode for operating the movable object from a normal mode to a safe mode, wherein the safe mode is selected from the normal mode, the safe mode, and an interactive mode;
in response to detecting the user not being within the proximity of the movable object, operating the movable object in the normal mode;
applying a control scheme associated with the safe mode to control the operation of the movable object, the control scheme using one or more control components to control a set of movement characteristics; in response to the movable object being in the safe mode, limiting control gain for at least one control component of the one or more control components; and
in response to an indication that the user intends to interact with the movable object, switching the operating mode for operating the movable object to the interaction mode, wherein the interaction mode supports interaction between the user and the movable object by one or more of the following: supporting the user to freely rotate the camera of the movable object to a random direction, allowing the user to freely rotate the movable object to a specific direction, or freely moving the movable object to a designated position.

2. The method of claim 1, further comprising:
receiving a signal from a remote device, wherein the signal indicates whether the user is within the proximity of the movable object.

3. The method of claim 1, further comprising:
detecting a change of an environment, which indicates whether the user is within the proximity of the movable object.

4. The method of claim 1, wherein the one or more control components include one or more of:
a position control component to perform position control,
a velocity control component to perform velocity control,
an orientation control component to perform orientation control, and
a tilt control component to perform tilt control.

5. The method of claim 4, further comprising:
maintaining the tilt control while relaxing the position control, the velocity control, and the orientation control.

6. The method of claim 1, further comprising:
applying a first component operation mode when the live object is detected within the proximity of the movable object, and applying a second component operation mode when no live object is detected within the proximity of the movable object, and wherein the first component operation mode and the second component operation mode are different.

7. The method of claim 1, further comprising:
applying a first payload operation mode when the live object is detected within the proximity of the movable object, and applying a second payload operation mode when no live object is detected within the proximity of the movable object, and wherein the first payload operation mode and the second payload operation mode are different.

8. The method of claim 1, further comprising:
controlling the movable object to maintain a hovering state when the live object is detected within the proximity of the movable object.

9. The method of claim 1, wherein the operation mode further comprises: a ready-to-interact mode.

10. The method of claim 9, further comprising:
allowing the movable object to have a yaw movement when the movable object is operating in the interactive mode.

11. The method of claim 10, further comprising:
maintaining the movable object in a horizontal attitude when the movable object is in the interactive mode.

12. A system for controlling a movable object, comprising:
one or more microprocessors; and
a storage medium storing instructions that, when executed by the one or more microprocessors, cause the one or more microprocessors to:
determine whether a user of the movable object is within a proximity of the movable object;
in response to detecting the user being within a proximity of the movable object, switch an operation mode for operating the movable object from a normal mode to a safe mode, wherein the safe mode is selected from the normal mode, the safe mode, and an interactive mode;
in response to detecting the user not being within the proximity of the movable object, operate the movable object in the normal mode;
apply a control scheme associated with the safe mode to control the operation of the movable object, the control scheme using one or more control components to control a set of movement characteristics; in response to the movable object being in the safe mode, limit control gain for at least one control component of the one or more control components; and
in response to an indication that the user intends to interact with the movable object, switch the operating mode for operating the movable object to the interaction mode, wherein the interaction mode supports interaction between the user and the movable object by one or more of the following: supporting the user to freely rotate the camera of the movable object to a random direction, allowing the user to freely rotate the movable object to a specific direction, or freely moving the movable object to a designated position.

13. The system of claim 12, wherein:
the instructions further cause the one or more processors to apply a first component operation mode when the live object is detected within the proximity of the movable object, and apply a second component operation mode when no live object is detected within the proximity of the movable object, and wherein the first component operation mode and the second component operation mode are different; and/or
the instructions further cause the one or more processors to apply a first payload operation mode when the live object is detected within the proximity of the movable object, and apply a second payload operation mode when no live object is detected within the proximity of the movable object, and wherein the first payload operation mode and the second payload operation mode are different.

14. An unmanned aerial vehicle (UAV), comprising:
one or more sensing devices that collect information from a surrounding area of the UAV; and
one or more processors configured to:
determine whether a user of the UAV is within a proximity of the UAV;
in response to detecting the user being within the proximity of the UAV, switch an operation mode for operating the UAV from a normal mode to a safe mode, wherein the safe mode is selected from the normal mode, the safe mode, and an interactive mode;
in response to detecting the user not being within the proximity of the UAV, operate the UAV in the normal mode;
apply a control scheme associated with the safe mode to control the operation of the UAV, the control scheme using one or more control components to control a set of movement characteristics; in response to the UAV being in the safe mode, limit control gain for at least one control component of the one or more control components; and
in response to an indication that the user intends to interact with the UAV, switch the operating mode for operating the UAV to the interaction mode, wherein the interaction mode supports interaction between the user and the UAV by one or more of the following: supporting the user to freely rotate the camera of the UAV to a random direction, allowing the user to freely rotate the UAV to a specific direction, or freely moving the UAV to a designated position.

* * * * *